United States Patent [19]

Crum et al.

[11] 4,384,985
[45] May 24, 1983

[54] CATALYST COMPOSITION FOR PRODUCING TERTIARY-BUTYLSTYRENE

[75] Inventors: Glen F. Crum; Samuel J. Paton, both of Odessa, Tex.

[73] Assignee: El Paso Products Company, Odessa, Tex.

[21] Appl. No.: 345,033

[22] Filed: Feb. 2, 1982

[51] Int. Cl.³ .............................................. B01J 27/14
[52] U.S. Cl. ..................................... 252/437; 252/435
[58] Field of Search ................................ 252/435, 437

[56] References Cited

U.S. PATENT DOCUMENTS

| | | | |
|---|---|---|---|
| 2,349,243 | 5/1944 | Bates | 252/437 |
| 2,449,050 | 9/1948 | Bond et al. | 252/437 |
| 3,088,908 | 5/1963 | Hansford | 252/435 X |
| 3,297,587 | 1/1967 | Scherhaf et al. | 252/435 X |
| 3,297,778 | 1/1967 | Noddinji et al. | 252/435 X |
| 3,299,155 | 1/1967 | Adams | 585/444 X |
| 3,409,696 | 11/1968 | Mennis et al. | 252/437 X |
| 3,416,884 | 12/1968 | Stynes et al. | 252/437 |
| 3,421,948 | 1/1969 | Webb et al. | 252/437 X |
| 3,615,807 | 10/1971 | Yates | 252/437 X |
| 3,733,327 | 5/1973 | Vrieland et al. | 252/437 X |
| 3,905,914 | 9/1975 | Jurewicz et al. | 252/437 |
| 3,932,549 | 1/1976 | Kominani et al. | 585/438 |
| 3,957,897 | 5/1976 | Vrieland et al. | 585/444 X |

*Primary Examiner*—Delbert E. Gantz
*Assistant Examiner*—William G. Wright
*Attorney, Agent, or Firm*—Depaoli & O'Brien

[57] ABSTRACT

This invention provides an improved oxydehydrogenation process for the production of tertiary-butylstyrene which involves the contacting of a vapor phase mixture of tertiary-butylethylbenzene and oxygen with a novel coprecipitated nickel-zirconium phosphate or nickel-zirconium-cerium phosphate catalyst composition.

The tertiary-butylstyrene is produced with a high conversion selectivity, and concomitantly there is little or no dialkenylbenzene byproducts produced.

3 Claims, No Drawings

CATALYST COMPOSITION FOR PRODUCING TERTIARY-BUTYLSTYRENE

BACKGROUND OF THE INVENTION

Alkenyl-substituted aromatic compounds are important starting materials for the production of resins, plastics, rubbers, solvents, chemical intermediates, and the like.

Processes for the production of alkenyl-substituted aromatic compounds often are characterized by low conversion rates which necessitate the recycle of large quantities of unconverted charge. Many of the known processes require the presence of a large volume of steam or other gaseous diluent which is a cost disadvantage. In some processes the conversion efficiency to alkenyl-substituted aromatic product is diminished because of the formation of a relatively large proportion of carbon oxides and other byproducts.

In one well-known commercial process, $C_2-C_3$ alkylaromatic hydrocarbons (e.g., ethylbenzene, ethyltoluene and isopropylbenzene) are converted to the corresponding styrene derivatives by passage of the alkylaromatic hydrocarbon feed and steam over a $Fe_2O_3$ catalyst. The conversion per pass is in the 35–40% range, and comparatively high temperatures are needed for the oxidative dehydrogenation reaction.

Illustrative of other oxidative dehydrogenation processes, U.S. Pat. No. 3,299,155 describes a process for the production of alkenylbenzenes which involves contacting a mixture of an ethyl (or isopropyl) substituted benzene compound and sulfur dioxide in vapor phase with a metal phosphate catalyst such as calcium phosphate.

U.S. Pat. No. 3,409,696 describes a process which involves contacting an admixture of $C_2-C_4$ alkylaromatic hydrocarbon and steam at a temperature of 500°–650° C. with a catalyst containing 20–60 weight percent of a bismuth compound (e.g., bismuth oxide) on a calcium phosphate support of which at least 90% of the total pore volume is contributed by pores having a diameter of 1000–6000 A.

U.S. Pat. No. 3,733,327 describes an oxydehydrogenation process for converting a $C_2-C_6$ alkylaromatic compound to the corresponding $C_2-C_6$ alkenylaromatic compound which comprises contacting an admixture of starting material and oxygen at 400°–650° C. with a cerium phosphate or cerium-zirconium phosphate catalyst.

U.S. Pat. No. 3,957,897 describes a process for oxydehydrogenation of $C_2-C_6$ alkylaromatic compounds which involves the use of oxygen, a reaction zone temperature of 450°–650° C., a space velocity of 55–2500, and a catalyst which is at least one of calcium, magnesium and strontium pyrophosphate.

More recently, there has been increasing concern with respect to the potentially harmful environmental effects associated with the manufacture of synthetic resin products. In the molding of large shaped articles, for example, volatile components of a polymerizable monomeric formulation sometimes tend to evaporate from freshly coated mold surfaces which are exposed.

Various means have been contemplated for reducing the level of fugitive vapors in a synthetic resin manufacturing plant. One method involves the replacement of volatile monomers of a formulation with monomers which have a lower vapor pressure. Thus, it is advantageous to substitute an alkenylaromatic compound such as tertiary-butylstyrene for styrene in a polymerizable formulation which contains the volatile styrene as a comonomer.

As a further consideration, it has been found that tertiary-butylstyrene is desirable as a comonomer in the preparation of copolymers or as a curing agent for fiber-reinforced plastics because it improves the moldability of polymerizable formulations and it lessens the mold shrinkage of molded plastic articles.

The advantages of tertiary-butylstyrene as a comonomer in resin systems has stimulated interest in improved processes for synthesizing this type of higher molecular weight alkenylaromatic compound.

U.S. Pat. No. 3,932,549 describes a process for preparing tertiary-butylstyrene which comprises reacting tertiary-butylbenzene with ethylene and oxygen at 50°–300° C. in the presence of a catalyst prepared by treating metallic palladium or a fatty acid salt thereof with pyridine.

Other known processes for producing tertiary-butylstyrene involve oxydehydrogenation of tertiary-butylethylbenzene. The type of patent processes described hereinabove for oxydehydrogenation of $C_2-C_6$ alkylaromatic compounds are generally applicable for conversion of tertiary-butylethylbenzene to tertiary-butylstyrene.

However, the chemical reactivity of tertiary-butylethylbenzene under oxydehydrogenation conditions is more complex than that of simpler chemical structures such as ethylbenzene or ethyltoluene. The tertiary-butyl substituent of tertiary-butylethylbenzene under oxydehydrogenation conditions is susceptible to cracking so as to yield methane and a residual isopropenyl substituent on the benzene nucleus.

Consequently, one of the ultimate byproducts of tertiary-butylethylbenzene oxydehydrogenation is a dialkenylbenzene derivative such as isopropenylstyrene.

Because of the presence of two or more polymerizable alkenyl groups, a compound such as isopropylstyrene tends to undergo crosslinking activity and form insoluble byproducts during the high temperature cycles of starting material conversion and product recovery in an oxydehydrogenation process. Heat exchangers and distillation columns can be rendered inoperative by the deposition of high molecular weight polymeric residues.

Further, the presence of an isopropenylstyrene type of contaminant, particularly a variable quantity of such material, in purified tertiary-butylstyrene can complicate or even prohibit the application of the contaminated tertiary-butylstyrene product as a comonomer in polymerizable formulations.

Accordingly, it is an object of the invention to provide a process for oxydehydrogenation of $C_2-C_6$ alkyl-substituted aromatic compounds to the corresponding alkenylsubstituted aromatic derivatives.

It is another object of this invention to provide a process for converting tertiary-butylethylbenzene to tertiary-butylstyrene under moderate conditions with a high level of starting material conversion and product selectivity.

It is another object of this invention to provide a process for converting tertiary-butylethylbenzene to tertiarybutyl-styrene with little or no production of dialkenylbenzene byproducts.

It is a further object of this invention to provide a novel catalyst adapted for oxydehydrogenation processes.

Other objects and advantages of the present invention shall become apparent from the accompanying description and examples.

DESCRIPTION OF THE INVENTION

One or more objects of the present invention are accomplished by the provision of a process which comprises contacting a feed stream containing tertiary-butylethylbenzene and oxygen in vapor phase with a catalyst comprising nickel-zirconium phosphate.

In a more specific embodiment, this invention provides a process for the production of tertiary-butylstyrene under oxydehydrogenation conditions which comprises contacting a feed mixture of tertiary-butylethylbenzene and oxygen at a temperature in the range between about 350° C. and 650° C. with a coprecipitated nickel-zirconium phosphate catalyst, wherein the conversion selectivity to tertiary-butylstyrene is at least 80 mole percent, and the conversion selectivity to dialkenylbenzene is essentially zero mole percent.

In another specific embodiment, this invention provides a process for the production of tertiary-butylstyrene under oxydehydrogenation conditions which comprises contacting a feed mixture of tertiary-butylethylbenzene and oxygen at a temperature in the range between about 350° C. and 650° C. with a coprecipitated nickel-zirconium-cerium phosphate catalyst, where the conversion selectivity to tertiary-butylstyrene is at least 80 mole percent, and the conversion selectivity to dialkenylbenzene is essentially zero mole percent.

A preferred reaction temperature for the oxydehydrogenation reaction is one which is in the range between about 400° C. and 600° C.

The feed admixture of tertiary-butylethylbenzene and oxygen can contain quantities of other hydrocarbons which do not adversely affect the invention oxydehydrogenation reaction, e.g., hydrocarbons such as paraffins and/or olefinic hydrocarbons which may be present in commercially available alkylbenzenes.

The molecular oxygen component of the feed admixture preferably is present in a quantity between about 0.2–5 moles per mole of tertiary-butylethylbenzene, and most preferably in a molar ratio of 0.8–2:1. The oxygen can be supplied as air, commercially pure oxygen, or air enriched with oxygen.

It is advantageous to include a gasiform diluent in the feed stream. Illustrative of suitable diluents are carbon dioxide, nitrogen, noble gases and steam, either individually or in admixture. The diluent is normally employed in a quantity between about 2–20 moles per mole of tertiary-butylethylbenzene in the feed stream.

The pressure utilized in the vapor phase oxydehydrogenation process can be subatmospheric, atmospheric or superatmospheric. A convenient pressure for the vapor phase process is one which is in the range between about 1 and 200 psi.

Suitable reactors for the vapor phase process include either fixed bed or fluid bed reactors which contain the invention nickel-zirconium phosphate or nickel-zirconium-cerium phosphate catalyst composition. The process can be conducted continuously or noncontinuously, and the catalyst may be present in various forms such as a fixed bed or a fluidized system.

The residence time (i.e., catalyst contact time) of the feed stream in the vapor phase process will vary in the range of about 0.5–20 seconds, and preferably will average in the range between about 1–15 seconds. Residence time refers to the contact time adjusted to 25° C. and atmospheric pressure. The contact time is calculated by dividing the volume of the catalyst bed (including voids) by the volume per unit time flow rate of the feed stream at NTP.

An important aspect of the present invention process is the use of a novel coprecipitated nickel-zirconium phosphate or nickel-zirconium-cerium phosphate catalyst composition. The catalyst exhibits unique properties for the conversion of tertiary-butylethylbenzene to the tertiary-butylstyrene with a high conversion efficiency, and with little or no production of dialkenylbenzene type of byproducts. The addition of a cerium metal component to a nickel-zirconium phosphate catalyst appears to enhance the reactivity and selectivity of the catalyst for conversion of tertiary-butylethylbenzene to tertiary-butylstyrene.

The atomic ratio of metals in the catalyst composition can vary in the range of about 5–20:1:0–1 of nickel:zirconium:cerium. The phosphate component is present in a quantity at least sufficient to satisfy the valences of the metal elements in the catalyst.

The catalyst can be prepared by the admixture of a phosphate compound (e.g., phosphoric acid) with water-soluble compounds of nickel, zirconium (and cerium) metals, respectively. Illustrative of water-soluble or partially water-soluble compounds are the chlorides, nitrates and sulfates of nickel, zirconium and cerium.

In a preferred procedure, the pH of the resultant solution of nickel, zirconium, (cerium) and phosphate compounds is adjusted to about 7 with an alkaline reagent such as ammonium hydroxide. The coprecipitate which forms is recovered, washed with water, and dried.

It has been found that the activity of the catalyst composition is enhanced if the coprecipitate preparation is calcined in an inert atmosphere at a temperature between about 300° C. and 600° C. for a period of about 1–24 hours.

The coprecipitated nickel-zirconium phosphate or nickel-zirconium-cerium phosphate composition described above can be used as the catalyst per se, or the said composition can be combined with a suitable internal diluent or carrier substrate. The carrier substrate is preferably incorporated during the coprecipitate formation step of the catalyst preparation.

The carrier substrate should be relatively refractory to the conditions utilized in the invention process. Suitable carrier substrate materials include (1) silica or silica gel, silicon carbide, clays, and silicates including those synthetically prepared and naturally occurring, which may or may not be acid treated such as attapulgus clay, china clay, diatomaceous earth, Fuller's earth, kaolin, asbestos and kieselguhr; (2) ceramics, porcelain, crushed firebrick and bauxite; (3) refractory inorganic oxides such as alumina, titanium dioxide, zirconium dioxide, chromium oxide, beryllium oxide, vanadium oxide, cesium oxide, hafnium oxide, zinc oxide, molybdenum oxide, bismuth oxide, tungsten oxide, uranium oxide, magnesia, boria, thoria, silica-alumina, silica-magnesia, chromia-alumina, alumina-boria and silica zirconia; (4) crystalline zeolitic alumino-silicates such as naturally occurring or synthetically prepared mordenite and/or faujasite, either in the hydrogen form or in a form which has been treated with multivalent cations;

and (5) spinels such as $MgAl_2O_4$, $FeAl_2O_4$, $ZnAl_2O_4$, $MnAl_2O_4$, $CaAl_2O_4$, and other like compounds having the formula $MO.Al_2O_3$ where M is a metal having a valence of 2.

The catalyst as employed in the invention process can be in the shape of granules, pellets, extrudate, powders, tablets, fibers, or other such convenient physical form.

A preferred catalyst composition of the present invention is one which corresponds to the formula:

$$Ni_{5.20}Zr_1Ce_{0.1}(PO_4)_x$$

wherein x is a number sufficient to satisfy the valences of the metal components.

The preferred catalyst composition of the present invention is adapted for oxydehydrogenation of hydrocarbon compounds such as $C_3$–$C_{10}$ alkenes, $C_4$–$C_{10}$ cycloalkenes and $C_2$–$C_6$ alkylaromatic compounds, and has particular advantage for the oxydehydrogenation of tertiary-butylethylbenzene and ethyltoluene under mild oxidation conditions.

The presence of the cerium metal component in an invention nickel-zirconium-cerium phosphate catalyst composition appears to enhance the reactivity and extend the life of the catalyst under hydrocarbon oxydehydrogenation conditions.

The following examples are further illustrative of the present invention. The reactants and other specific ingredients are presented as being typical, and various modifications can be derived in view of the foregoing disclosure within the scope of the invention.

EXAMPLE I

This Example illustrates the preparation and application of a nickel-zirconium phosphate oxidation catalyst.

A.

A slurry is prepared by admixing 10 grams of zirconium nitrate (0.04 M) with 50 grams of water, and adding phosphoric acid (1.3 M) with stirring. A solution of 11.6 grams of nickel nitrate (0.04 M) in 20 grams of water is added to the slurry, and the slurry admixture pH is adjusted to 7 with ammonium hydroxide.

An additional 105 gram quantity of nickel nitrate (0.36 M) in 100 grams of water is added slowly with stirring to the slurry admixture, then the pH of the slurry is adjusted to 7.2 with ammonium hydroxide.

The slurry is heated to a temperature of about 50° C., maintained at that temperature for a period of about one hour, and then cooled to room temperature. The solid catalyst precursor which has precipitated is separated by filtration. The recovered catalyst precursor is washed with water, and then dried in a vacuum oven at 120° C. The dried catalyst precursor is calcined at 550° C. under a nitrogen atmosphere for a period of 5 hours.

When a carrier substrate is being employed, it is preferably incorporated during the initial aqueous slurry admixture stage.

B.

A portion of the nickel-zirconium phosphate catalyst is ground and sieved to a mesh size in the range of 10–20. A 1 cm³ quantity of the catalyst is charged to an electrically heated reactor, and the reactor is heated to a temperature of about 460° C.

An air flow of 10 milliliters/minute and a tertiary-butylethylbenzene flow of 1 milliliter/hour are introduced into the inlet of the reactor. The effluent stream from the reactor is cooled and the resultant liquid components are collected.

The percent conversion of tertiary-butylethylbenzene is 29, and the mole percent selectivity to tertiary-butylstyrene is 87.1. The relative selectivity yield of dialkenylbenzenes is less than about 0.28 mole percent.

EXAMPLE II

This Example illustrates the preparation and application of a nickel-zirconium-cerium phosphate oxidation catalyst.

In a manner similar to that described in Example I, phosphoric acid (1.3 M) is added to an aqueous slurry of 10 grams of zirconium nitrate (0.04 M), followed by the addition of 18 grams of cerium(III) nitrate (0.04 M). An aqueous solution of 117 grams of nickel nitrate (0.4 M) is added to the slurry, and the pH of the slurry medium is adjusted to about 7.2 with ammonium hydroxide.

The resultant slurry admixture is heated at a temperature of 50° C. for about one hour, and then cooled to room temperature. The precipitated solid catalyst precursor is recovered by filtration, dried in a vacuum oven at 120° C., and then calcined at 550° C. under a nitrogen atmosphere for a period of 5 hours.

Following the procedure of Example I, a feedstream of tertiary-butylethylbenzene and air is contacted at a temperature of about 450°–460° C. with the nickel-zirconium-cerium phosphate catalyst described above. The product effluent liquids and gases are analyzed by gas chromatographic analysis.

The percent conversion of tertiary-butylethylbenzene is 43, and the mole percent selectivity to tertiary-butylstyrene is 87.8. The relative selectivity yield of dialkenylbenzenes is less than about 0.16 mole percent.

When a nickel-zirconium-cerium phosphate catalyst contains Ce(IV) rather than Ce(III) metal component, the yield of dialkenylbenzene byproducts tends to increase.

EXAMPLE III

A nickel-zirconium-cerium phosphate catalyst is prepared in the same manner as Example II, employing a three-fold increase in the relative proportions of chemical components.

A 100 cm³ portion (62 grams) of the catalyst powder (10–20 mesh) is charged to a reactor which is a 0.5 inch stainless steel pipe of 24 inch length. The reactor and part of the feed line are immersed in a molten salt bath.

The feed stream is a blend of 86 grams/hour of tertiary-butylethylbenzene, 750 milliliters/minute of air, and 1100 milliliters/minute of nitrogen, and the peak temperature in the oxidation reaction zone is about 490° C.

The percent conversion of tertiary-butylethylbenzene is 34, and the mole percent selectivity to tertiary-butylstyrene is 86.4. Gas chromatographic analysis of the effluent product mixture does not indicate the presence of any dialkenylbenzene compounds.

When ethyltoluene is substituted for tertiary-butylethylbenzene in the above described oxidation process, a mole percent selectivity to vinyltoluene of at least 80 is obtained.

What is claimed is:

1. A coprecipitated catalyst composition adapted for oxydehydrogenation reactions, which catalyst corresponds to the formula:

$$Ni_{5.20}Zr_1Ce_{0.1}(PO_4)_x$$

wherein x is a number sufficient to satisfy the valences of the metal elements in the catalyst.

2. A coprecipitated catalyst composition in accordance with claim 1 wherein the cerium metal is substantially in the plus three valence state.

3. A coprecipitated catalyst composition in accordance with claim 1 in combination with a carrier substrate.

* * * * *